US00PP11654P

United States Patent [19]

Asako

[11] Patent Number: Plant 11,654

[45] Date of Patent: Nov. 28, 2000

[54] DOGWOOD TREE NAMED 'WHITE LOVE'

[75] Inventor: Mitsuo Asako, Urawa, Japan

[73] Assignees: Sumitomo Forestry Co., Ltd., Osaka; Sumitomo Forestry Landscaping Co., Ltd., Tokyo, both of Japan

[21] Appl. No.: 09/159,090

[22] Filed: Sep. 23, 1998

[30] Foreign Application Priority Data

Mar. 27, 1998 [JP] Japan ..... 10711

[51] Int. Cl.[7] ..... A01H 5/00

[52] U.S. Cl. ..... Plt./220

[58] Field of Search ..... Plt./220

[56] References Cited

U.S. PATENT DOCUMENTS

P.P. 1,710 5/1958 Hawkersmith ..... Plt./220

P.P. 2,112 12/1961 Chase ..... Plt./220

P.P. 4,242 4/1978 Blow et al. ..... Plt./220

P.P. 8,213 4/1993 Orton, Jr. et al. ..... Plt./220

OTHER PUBLICATIONS

Wandell, Willet N. Handbook of Landscape Tree Cultivars; East Prairie Publishing Co., Gladstone, IL 1989; pp. ix–x and pp. 41–42, 1989.

*Primary Examiner*—Howard J. Locker
*Assistant Examiner*—Wendy A Baker
*Attorney, Agent, or Firm*—Young & Thompson

[57] ABSTRACT

A distinctive Dogwood variety of the *Cornus florida L.* genus and species exhibits an upright growth pattern and is easily cultivated, with improved mildew resistance, more upright carriage, and increased size of inflorescence including involucre, as compared to either the 'Cloud Nine' or 'Cherokee Chief' varieties.

2 Drawing Sheets

BACKGROUND OF THE INVENTION

This invention relates to a new cultivar of dogwood tree of the genus Cornus, species *florida L,* identified as 'White Love'.

From seeds planted in 1986 in Saitama-ken, Japan, characteristics of a plant produced by chance which reached two meters in height were continuously observed since October of 1988. The instant variety was discovered in October, 1990 from one such plant and was stably reproduced asexually in Urawa, Saitama Prefecture, Japan, in February of 1991 by grafting in a quantity of 200. The characteristics of these trees were closely examined from March 1994 through February 1998. The trees in question were considered for their upright growth pattern to increase cultivation density, as well as ease of cultivation and aesthetic value.

SUMMARY OF THE INVENTION

The instant tree grows upright to an extremely great height at a rate of approximately 0.9 m per year. The branches have a large diameter and are brown in color, with no pattern, producing green shoots. The leaves are oval with acute tips and round bases. In maturity, the leaves are green with a medium gloss, turning red-orange in autumn. The inflorescence is an upward facing capitulum. The inflorescence including involucre is extremely large with a one-fold blossom. There are four involucral bracts which are long and wide, the yellow-white in color. The bracts open flat and remain so through maturity. The fruits are oval and somewhat longer and narrower than those of 'Cloud Nine'. The age of flowering, bloom, and time of flowering are all medium. Resistance to heat and cold is medium. Resistance to mildew is good.

Compared to the 'Cloud Nine' variety (U.S. Plant Pat. No. 2,112), the tree is taller and more upright. Additionally, the size of the inflorescence including involucre is greater. Mildew resistance is also improved.

Compared to the 'Cherokee Chief' variety (U.S. Plant Pat. No. 1,710), the instant tree is more upright. The angle of the branch-intermediate portion to the trunk is smaller. The color of the involucral bract is yellow-white (J.H.S. C.C. No. 2701) (R.H.S. 156D) and the size of the inflorescences including involucre is larger. Additionally, the involucres have less twist. Mildew resistance is excellent.

BRIEF DESCRIPTION OF THE DRAWINGS

The new variety of Cornus is illustrated in the accompanying color photographs.

The first drawing illustrates a close-up view of the flower.

The second drawing illustrates a wider view, encompassing a number of flowers.

The third drawing illustrates an entire tree in full bloom.

The fourth drawing illustrates an entire tree without foliage.

Color notations refer to the color charts of the Japan Horticultural Society (J.H.S. C.C.), Royal Horticultural Society (R.H.S.), and ISCC-NBS Centroid Color Charts (ISCC-NBS).

DETAILED DESCRIPTION OF THE INVENTION

Plant:

*Carriage.*—Upright with narrowly pyramidal crown.

*Height.*—Approximately 7 meters at 10 years of age.

Branch:

*Diameter.*—Large (4.1 mm on average).

*Color shoot.*—Green.

*Color of branches.*—Brown.

*Surface pattern (marking or figure) of branches.*—None.

*Ramification.*—Medium.

*Length of internode.*—Medium (8.3 cm on average).

Leaves:

*Whole shape.*—Oval shape.

*Shape of tips.*—Acute.

*Shape of leaf bases.*—Round.

*Shape of margin.*—Entire.

*Curvature.*—Plane.
*Undulation of margin.*—Undulating.
*Blade.*—A little longer than that of 'Cloud Nine' (15.1 cm on average).
*Width.*—A little wider than that of 'Cloud Nine' (9.7 cm on average).
*Thickness.*—Medium.
*Color of new bud.*—Dark yellow green (J.H.S. C.C. No. 3507) (R.H.S. 144A).
*Color of new leaf.*—Dark yellow green (J.H.S. C.C. No. 3507) (R.H.S. 144A).
*Color of upper surface of mature leaves.*—Dark yellow green (J.H.S. C.C. No. 3508) (R.H.S. 146A).
*Color of lower surface of mature leaves.*—Gray green (J.H.S. C.C. No. 4913) (ISCC-NBS 156, dark greenish gray).
*Changeability of leaf color.*—No change between new leaf and mature leaf prior to change to autumn color.
*Color of autumn leaves.*—Intermediate of red and orange.
*Spots.*—None.
*Gloss.*—Medium.
*Hairs on the upper surface.*—Medium.
*Hairs on the lower surface.*—Medium.
*Veins.*—Easily visible.
*Diameter of petiole.*—Medium (2.1 mm on average).
*Length of petiole.*—Medium (1.1 cm on average).
*Color of petiole.*—Green.

Flower:
*Type of inflorescence.*—Capitulum.
*Direction of inflorescence.*—Upward facing.
*Size of inflorescence (capitulum).*—Medium (16.3 mm on average).
*Size of inflorescence including involucral bracts.*—Extremely large (12.6 cm on average).
*Size of bud.*—Medium (5.0 mm on average).
*Color of bud.*—Green yellow.
*Flowering habit.*—Single-flowered.
*Overlying of involucre.*—Overlying.
*Shape of whole involucre.*—Obovate.
*Shape of tip of involucre.*—Concave.
*Length of involucral bract.*—Longer than that of 'Cloud Nine' (6.0 cm on average).
*Width of involucral bract.*—Wider than that of 'Cherokee Chief' (5.1 cm on average).
*Number of involucral bracts.*—Medium (4).
*Color of involucral bract.*—Yellow white (J.H.S. C.C. No. 2701) (R.H.S. 156D).
*Color of pistil.*—Pale green.
*Color of stamen.*—Yellow white.
*Diameter of peduncle.*—Medium (2.0 mm on average).
*Length of peduncle.*—Medium (4.0 cm on average).
*Color of peduncle.*—Pale green.

Fruits:
*Shape.*—Elliptical.
*Length.*—A little longer than that of 'Cloud Nine' (1.7 cm on average).
*Width.*—A little narrower than that of 'Cloud Nine' (1.2 cm on average).
*Color.*—Red.

Others:
*Scent of flower.*—None.
*Aptitude to bear fruit.*—Higher than that of 'Cloud Nine'.
*Age of flowering.*—Precocious compared to 'Cherokee', late-blooming compared to 'Cloud Nine'.
*Scale of flowering.*—Medium.
*Blooming.*—Blooms once per year, with first bloom observed April 20, last bloom observed May 5.
*Time of flowering.*—Medium.
*Defoliation.*—Deciduous.
*Cold resistance.*—Medium (to −25° C.).
*Heat resistance.*—Medium (to 40° C.).
*Disease resistance.*—Strong, particularly to powdery mildew.

*Time of fruit maturity.*—Mid-November.

Branches:
*The angle of the intermediate portion of a branch to the trunk in the intermediate portion of tree.*—29.7° on average.

I claim:

1. The new and distinct variety of dogwood tree, as described and illustrated.

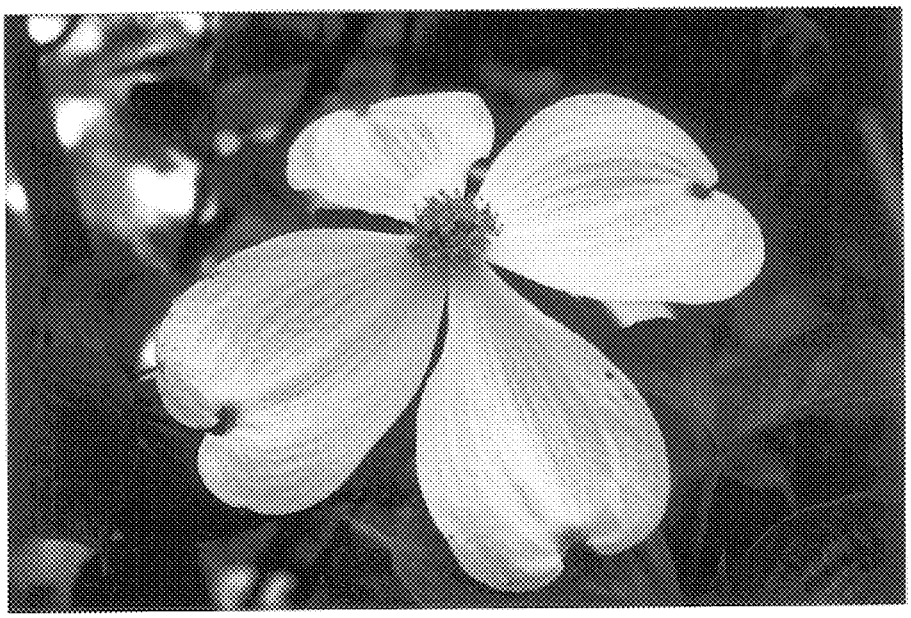
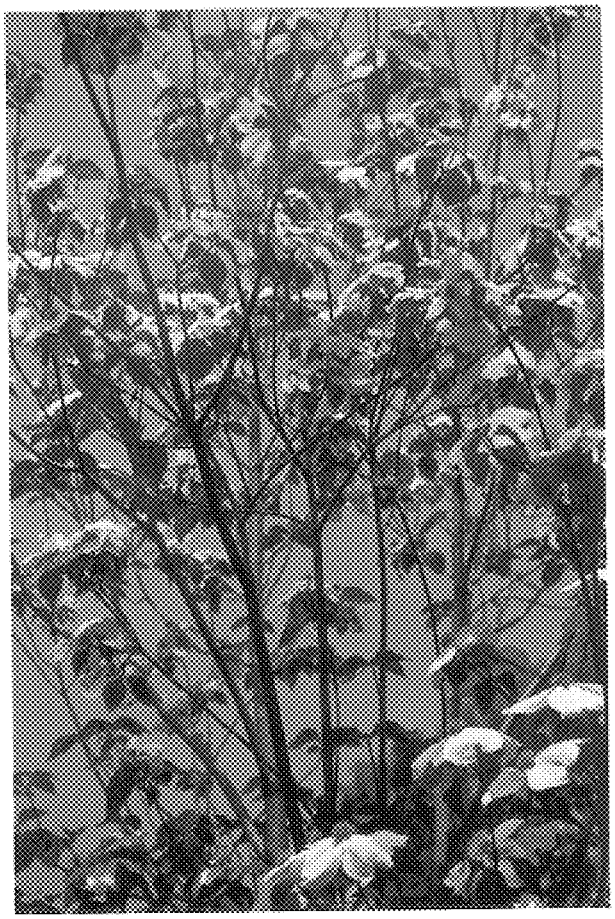

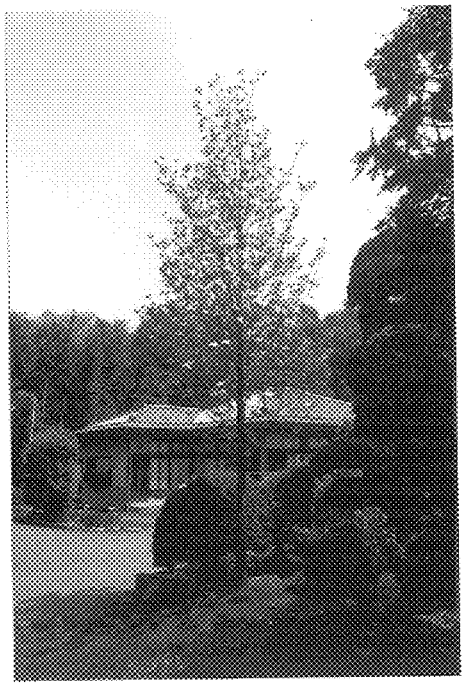
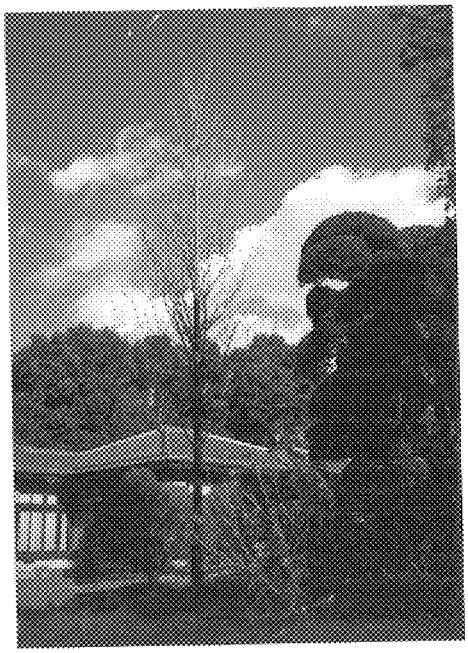

* * * * *